United States Patent [19]

Folkman et al.

[11] Patent Number: 5,135,919
[45] Date of Patent: Aug. 4, 1992

[54] METHOD AND A PHARMACEUTICAL COMPOSITION FOR THE INHIBITION OF ANGIOGENESIS

[75] Inventors: Judah Folkman, Brookline, Mass.; Takeshi Fujita, Takarazuka, Japan; Donald Ingber, Boston, Mass.; Tsuneo Kanamaru, Takatsuki, Japan

[73] Assignees: Children's Medical Center Corporation, Boston, Mass.; Takeda Chemical Industries, Ltd., Japan

[21] Appl. No.: 173,305

[22] Filed: Mar. 25, 1988

Related U.S. Application Data

[63] Continuation-in-part of Ser. No. 145,407, Jan. 19, 1988, abandoned.

[51] Int. Cl.$^5$ .................... A61K 31/715; A61K 31/70
[52] U.S. Cl. .......................... 514/56; 514/24; 514/58; 514/475
[58] Field of Search .............. 514/24, 56, 58, 475; 536/103

[56] References Cited

U.S. PATENT DOCUMENTS

| | | | |
|---|---|---|---|
| 2,803,586 | 8/1957 | Peterson et al. | 435/244 |
| 2,844,512 | 7/1958 | Eble | 514/24 |
| 3,232,833 | 2/1966 | Riviere | 514/54 |
| 4,727,064 | 2/1988 | Pitha | 536/103 |

OTHER PUBLICATIONS

Maevskii et al., *Chemical Abstracts*, 70:36365g (1969).
Semenov. et al., *Chemical Abstracts*, 61:1709h (1964).
R. Crum, *Science*, vol. 230, p. 1375 (1985).
Folkman, et al. Science 230:1375–1378 (1985).
Folkman, et al., Journal of Cell Biology, vol. 107, No. 6, part 3, p. 579a, Abstract No. 3277 (1988).
Taylor, et al., Nature, 297:307–312 (1982).
Tursunkhodzhaev. Chemical Abstracts, 63:2251e (1965).
J. Folkman; Advances in Cancer Research vol. 43, pp. 175–203 1985 ed. George Klein and Sidney Weinhouse.
Proc. Nat. Acad. Sci. USA, 48, 733–735 (1962).
Folkman, J. et al., J. Exp. Med., 133 275 (1971).
Kimura, M. et al., J. Pharmacobiol. Dyn., 9, 442 (1986).
Gimbrone, M. A. J. et al., J. Natl. Cancer Inst. 52, 413 (1974).
DiPaolo, et al. (Carcinolytic Activity of Fumagillin) Antibiotics Annual; 541–546 (1958–1959).
The Merck Index Tenth Edition; 611–612 (1983).

*Primary Examiner*—Ronald W. Griffin
*Assistant Examiner*—Pamela S. Webber
*Attorney, Agent, or Firm*—Gregory D. Williams; David G. Conlin; David R. Resnick

[57] ABSTRACT

Fumagillin and its salts have an angiogenesis inhibiting activity and are useful for prophylaxis and treatment of diseases induced by abnormally stimulated neovascularization. The invention also provides certain pharmaceutical compositions comprising fumagillin or its salt, and an agent which potentiates angiogenesis inhibition such as heparin and sulfated cyclodextrins such as beta-cyclodextrin tetradecasulfate.

13 Claims, 1 Drawing Sheet

METHOD AND A PHARMACEUTICAL COMPOSITION FOR THE INHIBITION OF ANGIOGENESIS

This is a continuation-in-part application of U.S. Ser. No. 145,407, filed Jan. 19, 1988, now abandoned.

The present invention relates to methods of prophylaxis or treatment of angiogenesis-related diseases induced by abnormally stimulated neovascularization in mammals. The invention also relates to certain pharmaceutical compositions comprising fumagillin and potentiators of angiogenesis inhibition.

BACKGROUND OF THE INVENTION

Angiogenesis is a process by which new capillary blood vessels are formed. This process occurs normally, e.g., during ovulation and formation of the placenta. It also occurs pathologically in wound healing, as well as in a variety of diseases where uncontrolled or rampant capillary growth is the cause of extensive tissue damage. Examples of the latter are in ophthalmology: diabetic retinopathy, retrolental fibroplasia, corneal graft neovascularization, neovascular glaucoma, ocular tumors and trachoma, where neovascularization may lead to blindness; in dermatology: psoriasis and pyogenic granuloma; in pediatrics: hemangioma, angiofibroma, and hemophiliac joints; in surgery: hypertrophic scars, wound granulation and vascular adhesions; in internal medicine: rheumatoid arthritis, where new vessels in the joint may destroy articular cartilage and scleroderma; in cardiology: atherosclerotic plaque; and in cancer: many kinds of carcinomas and sarcomas, where progressive growth is dependent upon the continuous induction of angiogenesis by these tumor cells.

The realization that tumors, as well as many non-neoplastic diseases, are angiogenesis-dependent has led to a search for angiogenesis inhibitors that might be used therapeutically (See e.g., J. Folkman; Advances in Cancer Research Vol. 43, pp 175-203, 1985 ed. George Klein and Sidney Weinhouse).

Fumagillin is a known compound which has been used as an antimicrobial and antiprotozoal. Its physicochemical properties and method of production are well documented [Production; U.S. Pat. No. 2,803,586: Structure; Proc. Nat. Acad. Sci. USA, 48, 733-735 (1962)].

Fumagillin has a molecular formula of $C_{26}H_{34}O_7$. Its molecular weight is 458.53. Yellow needles from methanol extraction have an mp of about 194°–195° C. Fumagillin has the following structure:

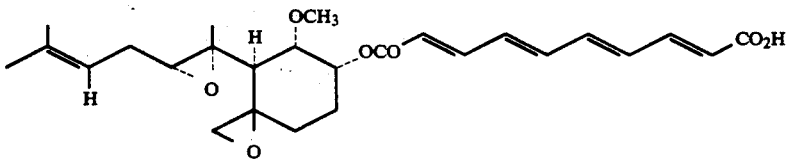

SUMMARY OF THE INVENTION

The present invention relates to the use of the fumagillin, obtainable from *Aspergillus fumigatus*, as an angiogenesis inhibitor. Fumagillin shows strong angiogenesis inhibitory activity and may be used to treat a variety of diseases induced by abnormally stimulated angiogenesis including diabetic retinopathy, trachoma, and the like. The present invention also relates to certain pharmaceutical compositions comprising fumagillin and agents which potentiate angiogenesis inhibition such as heparin and sulfated cyclodextrin, particularly beta cyclodextrin tetradecasulfate.

DETAILED DESCRIPTION OF THE INVENTION

Figure 1:
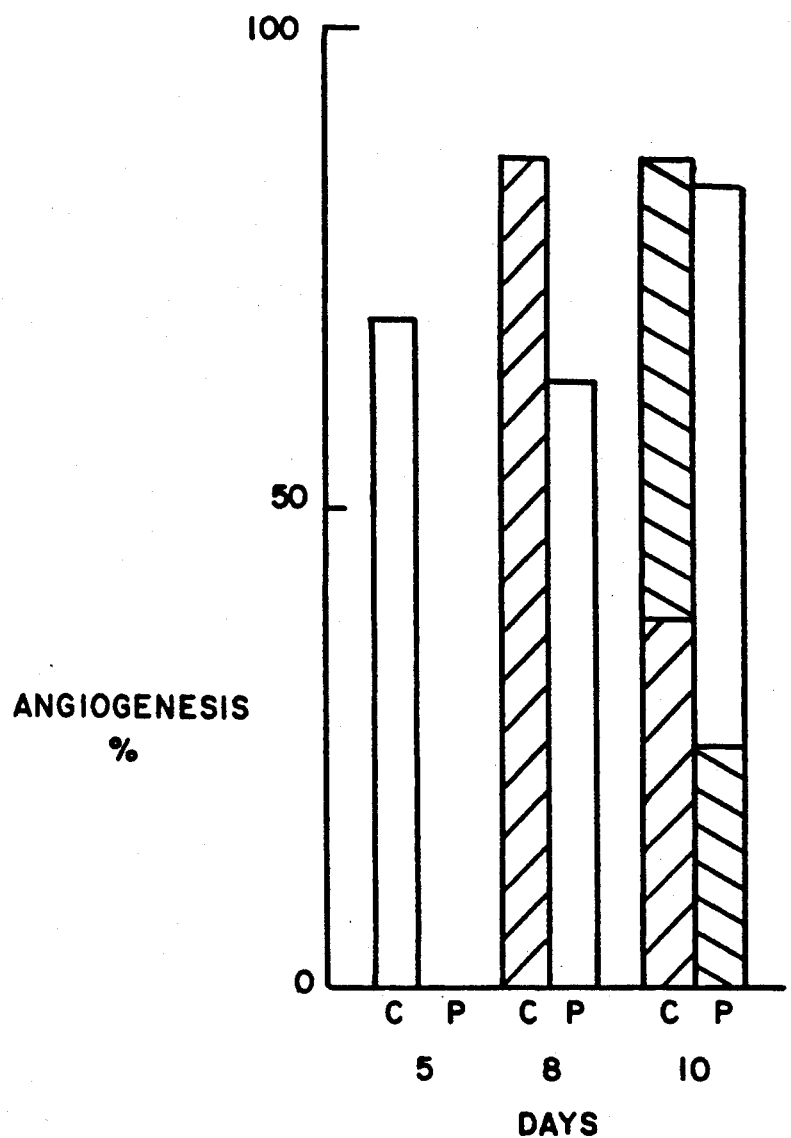
FIG. 1 illustrates the inhibition of neovascularization stimulated by bFGF by treatment with fumagillin in accordance with the rat corneal micropocket assay, which is disclosed in detail in Example 4.

The present invention provides novel methods for the treatment and/or prevention of angiogenesis-related diseases in mammals. The method, in its simplest form, comprises administering to the mammal an effective amount of fumagillin or a pharmaceutically acceptable salt thereof. The invention also provides certain pharmaceutical compositions comprising fumagillin or its salt, and an agent which potentiates angiogenesis inhibition such as heparin and sulfated cyclodextrins such as beta-cyclodextrin tetradecasulfate.

In accordance with the present invention, fumagillin has been found to be a strong inhibitor of angiogenesis in mammals. In treating angiogenesis-related diseases an effective amount of the free form, or a salt of fumagillin may be used. As the salt, inorganic salts such as alkali metal salt, e.g. sodium salt, potassium salt, alkaline-earth metal salt, e.g. calcium salt, and ammonium salt are preferred.

On the basis of its strong angiogenesis inhibitory activity, fumagillin and its salts are particularly useful for prophylaxis and treatment of diseases in the fields of ophthalmology, dermatology, pediatrics, surgery and cardiology.

Thus, fumagillin and its salts may be used for prophylaxis and/or treatment of neovascularization in diabetic retinopathy, retrolental fibroplasia, corneal graft neovascularization, neovascular glaucoma, ocular tumors, and trachoma; dermatological psoriasis and pyogenic granuloma; childrens hemangioma, angiofibroma and hemophiliac joints; and hypertrophic scars, wound granulation, vascular adhesions, rheumatoid arthritis, scleroderma and atherosclerotic plaque. Among these diseases, fumagillin and its salts are especially effective against diabetic retinopathy.

The use of fumagillin in accordance with the present invention has been found to be low in toxicity and is safely administered orally or parenterally to mammals (e.g. rat, rabbit, monkey, man) in forms of e.g. tablets, granules, capsules, injectable solutions, topical creams, and eye-drops.

To treat diabetic retinopathy, for example, fumagillin is administered orally in an amount of from about 1 mg/kg to 200 mg/kg per day, preferably in an amount of from about 2 mg/kg to 100 mg/kg per day. For oral administration, 5 mg to 100 mg of fumagillin or its salts may be formulated as a tablet or a capsule together with a pharmaceutically acceptable carrier, diluent or other suitable vehicle.

Fumagillin may also be administered subcutaneously or intravenously in an amount of from about 0.1 mg/kg to 20 mg/kg per day to an adult in the form of a pharmaceutical acceptable composition. Preferably, it is administered in an amount of from about 0.2 mg/kg to 10 mg/kg per day. The preferred form of fumagillin for intravenous administration is as a sodium salt.

Fumagillin may also be administered topically. For example, to treat eye-related angiogenesis diseases, fumagillin, especially as a salt, may be administered in the form of eye-drops. One to a few drops per dose is administered to the eye with a frequency of 1 to about 4 times a day according to the patient's condition. Preferably, the eye-drops are prepared by dissolving a fumagillin salt in distilled water to make a concentration of 0.001 to 3% (w/v). The solution also preferably contains an isotonizing agent, a preservative, or a thickening agent and is adjusted to a pH of from about 5 to 9.

In accordance with another aspect of the present invention, it has been found that certain agents potentiate the angiogenesis inhibitory activity of fumagillin. Such agents include heparin and a group of compounds known as sulfated cyclodextrins.

Heparin, an alpha, beta glycosidically linked highly sulfated copolymer of uronic acid and glycosamine, has been used clinically as an anticoagulant for half a century. Despite its importance and widespread use, both the exact structure of heparin and the precise nature by which it acts in blood anticoagulation have not been discovered. Much of the difficulty in determining the structure of heparin results from the fact that it is not a homogeneous well-defined substance. Heparin is polydisperse with a molecular weight range from 5,000 to 40,000. Within a given chain, there are structural variations such as the varying degrees of sulfation, N-acetylation and C-5 epimerization in the uronic acid residue.

Cyclodextrins are natural cyclic compounds consisting of six (alpha), seven (beta) or eight (gamma) D-glucose units. It has a donut-shaped molecular structure which provides a cavity whereby clathrates may form with guest molecules of suitable size. The interior of the cavity consists largely of uniformly spaced bridging acetal oxygen atoms. One end of the cavity is edged with —CH$_2$OH Groups (one per glucose unit) and the other rim is similarly edged with secondary —CHOH Groups. The cavity contains water molecules hydrogen bonded to the interior oxygen atoms.

The alpha, beta, and gamma cyclodextrin sulfate salts are all usable as potentiating agents of fumagillin in accordance with the present invention. Beta-cyclodextrin salts are such as beta-cyclodextrin tetradecasulfate are preferred.

As discussed in more detail below, the angiogenesis inhibitory activity of fumagillin is markedly potentiated by sulfated polysaccharides such as heparin and beta cyclodextrin tetradecasulfate.

Thus, such agents may be used in conjunction with fumagillin in the prophylaxis or treatment of angiogenesis-related diseases. As the skilled artisan will appreciate, the relative amount of such potentiating agents to fumagillin may vary depending on a number of factors, including the patient's condition and administration route. In general, the ratio of potentiating agent to fumagillin by weight is between about 1:10 to 30:1, preferably from about 1:3 to 10:1.

The invention will be further illustrated with reference to the following examples which will aid in the understanding of the present invention, but which are not to be construed as a limitation thereof.

EXAMPLE 1

Shell-less Chorioallantoic Membrane Assay

The shell-less chorioallantoic membrane (CAM) assay was carried out by the method of Taylor and Folkman (S. Taylor and J. Folkman; Nature, 297, 307 (1982)) with a slight modification as follows: 3-days chick embryos were removed from their shells and cultured in plastic cups on hammocks of plastic wrap. The sodium salt of fumagillin 10 ug, along with acidic FGF 200 ng (bovine brain, R & D Systems, Inc.), and methylcellulose 30 ug (Fisher Scientific Co., 4000 centipoise) was placed on plastic disks (polypropylene, 6 mm in diameter). After the solution had dried, the disks were placed on the CAM of 10-day embryos. Three days later, inhibition of neovascular formation by fumagillin was observed under a stereoscope (X 20, SMZ-10, Nikon), and compared to the control disk containing acidic FGF 200 ng as a stimulant of angiogenesis and methylcellulose 30 ug without fumagillin. Fumagillin showed angiogenesis inhibitory activity by the CAM assay (Table 1).

TABLE 1

| Angiogenesis inhibitory activity of fumagillin by CAM assay. |  |
| --- | --- |
| Number of disk showing angiogenesis inhibition/number of disk tested |  |
| Exp. 1 | 3/3 |
| Exp. 2 | 2/6 |
| Exp. 3 | 6/9 |

EXAMPLE 2

Shell-less Chorioallantoic Membrane Assay

The shell-less chorioallantoic membrane (CAM) assay was carried out by the method of Folkman et al. (R.Crum. S.Szabo and J.Folkman; Science. 230. 1375 (1985)) as follows: three-day chick embryos were removed from their shells to petri dishes (Falcon 1005) under sterile hood and cultured for further 3 days.

The sodium salt of fumagillin and/or sulfated polysaccharide (e.g. heparin, beta cyclodextrin tetradecasulfate) were dissolved to a 0.45% methylcellulose aqueous solution and aliquots of 10 ul were pipetted onto Teflon rods. After the solution had dried, the methylcellulose disks (about 2 mm in diameter) containing test compounds, thus prepared, were implanted on the CAM of 6-day embryos.

After cultures for 48–72 hours, formations of avascular zones around the disks were observed with a stereoscope.

Percent of avascular zones was calculated by counting the disks forming avascular zones per the total disks tested. In each group there were 8–16 embryos.

As shown in Table 2, Fumagillin showed strong angiogenesis inhibitory activity by the CAM assay. Angiogenesis inhibitory activity of fumagillin was markedly potentiated by sulfated polysaccharides: heparin and beta cyclodextrin tetradecasulfate. Hydrocortisone does not potentiate and may suppress the effects of fumagillin.

TABLE 2

Angiogenesis inhibitory activity of fumagillin and potentiation by sulfated polysaccharides.

| compound tested/disk | | percent of avascular zones |
|---|---|---|
| fumagillin sodium salt | 50 ug | 57% |
| | 40 ug | 72% |
| | 30 ug | 62% |
| | 20 ug | 66% |
| | 10 ug | 75% |
| fumagillin sodium salt + hydrocortisone | 10 ug 60 ug | 40% |
| fumagillin sodium salt + heparin | 10 ug 50 ug | 100% |
| fumagillin sodium salt | 5 ug | 40% |
| fumagillin sodium salt + beta cyclodextrin tetradecasulfate | 5 ug 25 ug | 70% |

EXAMPLE 3

Mouse dorsal air sac assay

The angiogenesis assay by mouse dorsal air sac method (MDA) was carried out by the method below which is a modification of the original rat dorsal air sac assay developed by Folkman et al. (Folkman, J. et al.; J.Exp.Med.,133, 275 (9171)). Specifically, millipore chambers, equipped with a millipore filter with a pore size of 0.45 um (Millipore Corp.), were filled with $5 \times 10^6$ sarcoma 180 cells in 0.15 ml of saline. The control contained the same volume of saline.

Under Nembutal anesthesia, each mouse received both the control and the tumor cell-containing chambers in their dorsal air sac produced by the method mentioned above. Fumagillin was subcutaneously administered to the mice for 3 days after the day of operation as a solution or suspension in 0.5% arabic gum dissolved in saline. Unless otherwise specified, fumagillin was given at a dose of 100 mg (10 ml)/kg body weight. Four days later, the mice were given an intra arterial injection of carmine-gelatin solution under Nembutal anesthesia, and cooled on ice for about 2 hours to let the gelatin-containing blood form gels according to the method of Kimura (Kimura, M. et al.; J. Pharmacobiol. Dyn., 9, 442 (1986)). The skin was incised widely over the chambers and inner surface of the skin was exposed. The mouse fascia was observed under a stereoscope (X20; SMZ-10, Nikon). The anti-angiogenic activity of the compounds was evaluated by determining the extent of the tumor-induced vascular formation in mice administered the vehicle or the test compounds.

Tumor-induced vasculature exhibiting both coiling vessels and an increase of the vascular net was defined as positive angiogenesis.

As the results in Table 3 show, fumagillin effectively inhibited the tumor-induced vascular formation.

TABLE 3

Inhibition of angiogenesis induced by tumor cells by fumagillin

| | tumor-induced angiogenesis positive mice/total mice tested) |
|---|---|
| vehicle (arabic gum-saline) | 5/6 |
| fumagillin treated (100 mg/kg, s.c.) | 0/5 |

EXAMPLE 4

Rat corneal micropocket assay

The rat corneal micropocket assay was carried out essentially by the method of Gimbrone et al. (Gimbrone, M.A. Jr. et al., J. Natl. Cancer Inst. 52, 413(1974)). Corneal vascularization was induced in adult male rats of the Sprague-Dawley strain (Charles River, Japan) by implanting 500 ng of basic FGF (bovine, R & D Systems, Inc.) impregnated in EVA (ethylene-vinyl acetate copolymer) pellets in each cornea (n=5). On the same day, fumagillin (5 ug/pellet) was also impregnated in EVA and implanted into the same cornea between the FGF pellet and the limbus. Control rats received an implantation of the FGF pellet and the EVA pellet without fumagillin. Neovascular formation was observed under a stereoscope (X20, SMZ-10, Nikon). The extent of vascularization was graded from − to +++ (−, without neovascularization; +, positive neovascularization not yet reaching the FGF pellet; ++, positive neovascularization reaching the FGF pellet; +++, positive neovascularization surrounding the FGF pellet).

As shown in FIG. 1, neovascularization stimulated by bFGF was effectively inhibited by fumagillin.

EXAMPLE 5

In a similar experiment approximately 10 to 16 chick embryos (age 6 days) were used to assay each concentration of fumagillin substantially in accordance with the method described in Example 2. The fumagillin was applied in a 10 ul pellet to the chorioallantoic membrane with or without cyclodextrin. Forty-eight hours later, the percent of embryos with an avascular zone was recorded. The results are shown in Table 4. Unless otherwise indicated, the avascular zones are 1+, e.g., at least 2 mm in diameter. An avascular zone of 2+ equals 4 mm or greater in diameter, indicating very high activity. For example, 5 ug of fumagillin produced 33% avascular zones. In contrast, 5 ug of fumagilin plus 25 ug of beta-cyclodextrin tetradecasulfate produced 100% avascular zones (the majority of which are 2+). Cyclodextrin (25 ug) alone had no detectable effect. Heparin also potentiates fumagillin, but it is not as potent as beta-cyclodextrin in this respect (data not shown).

TABLE 4

| Fumagillin ug/10 ul | B Cyclodextrin tetradecasulfate ug/10 ul | Percent Avascular Zones |
|---|---|---|
| 50 | 0 | 57% |
| 40 | 0 | 72% |
| 30 | 0 | 62% |
| 20 | 0 | 75% |
| 10 | 0 | 75% |
| 5 | 0 | 33% |
| 2.5 | 0 | 40% |
| 1 | 0 | 0% |
| 5 | 25 | 100% (2+) |
| 2.5 | 25 | 57% |
| 1 | 25 | 33% |
| Fumagillin | Heparin | |
| 10 | 50 | 100% |

B cyclodextrin alone = 0% avascular zones.
Heparin alone = 0% avascular zones.

EXAMPLE 6

A pharmaceutical preparation for use as eye-drops was prepared as follows:

| | |
|---|---|
| fumagillin sodium salt | 1 g |
| boric acid | 16 g |
| sodium borate | 7 g |
| p-hydroxy-benzoic acid methylester | 0.25 g |
| p-hydroxy-benzoic acid propionylester | 0.15 g |

Sterile distilled water was added to total 1 liter. After sterilization by filtration, the solution was used as eye-drops.

EXAMPLE 7

A pharmaceutical preparation for use as eye-drops was prepared as follows:

| | |
|---|---|
| fumagillin sodium salt | 5 g |
| p-hydroxy-benzoic acid methylester | 0.25 g |
| p-hydroxy-benzoic acid propionylester | 0.15 g |
| dibasic sodium phosphate | 4. g |
| sodium chloride | 8.5 g |

Sterile distilled water was added to total 1 liter. The pH was adjusted to a pH 7.5. After sterilization by filtration, the solution was used as eye-drops.

What is claimed is:

1. A method of inhibiting angiogenesis in a mammal, comprising administering an amount of fumagillin effective for the inhibition of angiogenesis or a pharmaceutically acceptable salt thereof to the mammal.

2. A method of preventing angiogenesis in a mammal, comprising administering an amount of fumagillin effective for the prevention of angiogenesis or a pharmaceutically acceptable salt thereof to the mammal.

3. The method according to claim 1 or 2, wherein the angiogenesis is caused by abnormally stimulated neovascularization.

4. The method according to claim 3, wherein the abnormally stimulated neovascularization is diabetic retinopathy.

5. The method according to claim 3, wherein the abnormally stimulated neovascularization is trachoma.

6. The method according to claim 1 or 2, wherein fumagillin is administered orally in amount of 0.1 mg/kg to 200 mg/kg per day.

7. The method according to claim 1 or 2, wherein the fumagillin is administered intravenously in an amount of 0.1 mg/kg to 20 mg/kg per day.

8. The method according to claim 1 or 2, wherein an aqueous solution of fumagillin sodium salt at a concentration from 0.001% to 3% (w/v) is administered in the form of eye-drops.

9. The method of claim 1 or 2, further comprising administering in conjunction with fumagillin or a salt thereof, an effective amount of a potentiator of said fumagillin selected from heparin and a sulfated cyclodextrin, the ratio of potentiator to fumagillin by weight being between about 1:10 to 30:1.

10. The method of claim 9, wherein the sulfated cyclodextrin is beta cyclodextrin tetradecasulfate.

11. A pharmaceutical composition for the treatment of angiogenesis in mammals comprising fumagillin or a pharmaceutically acceptable salt thereof and a potentiator of said fumagillin selected from heparin and a sulfated cyclodextrin, the ratio o potentiator to fumagillin by weight being between about 1:10 to 30:1.

12. The pharmaceutical composition of claim 11, wherein the sulfated cyclodextrin is beta cyclodextrin tetradecasulfate.

13. The pharmaceutical composition of claim 11 or 12, further comprising a pharmaceutically acceptable carrier.

* * * * *

UNITED STATES PATENT AND TRADEMARK OFFICE
CERTIFICATE OF CORRECTION

PATENT NO. : 5,135,919

DATED : August 4, 1992

INVENTOR(S) : Folkman, et al.

It is certified that error appears in the above-identified patent and that said Letters Patent is hereby corrected as shown below:

On column 8, line 31, please change "ratio o" to --ratio of--.

Signed and Sealed this

Sixteenth Day of November, 1993

Attest:

BRUCE LEHMAN

Attesting Officer  Commissioner of Patents and Trademarks